United States Patent
O'Lenick, Jr. et al.

(10) Patent No.: US 6,582,686 B1
(45) Date of Patent: *Jun. 24, 2003

(54) WATER SOLUBLE CONDITIONING COMPLEXES

(75) Inventors: Anthony J. O'Lenick, Jr., Dacula, GA (US); Charles W. Buffa, Paterson, NJ (US)

(73) Assignee: Biosil Research Institute Inc, Paterson, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/973,587

(22) Filed: Oct. 9, 2001

Related U.S. Application Data

(63) Continuation-in-part of application No. 09/483,899, filed on Jan. 18, 2000, now Pat. No. 6,372,934.

(51) Int. Cl.$^7$ .............................. A61K 7/06; A61K 7/48
(52) U.S. Cl. ................. 424/70.27; 424/70.1; 424/70.11; 424/401; 560/89; 560/198
(58) Field of Search .................. 560/89, 198; 424/401, 424/70.1, 70.11, 70.27

(56) References Cited

U.S. PATENT DOCUMENTS

| | | |
|---|---|---|
| 5,296,625 A | 3/1994 | O'Lenick |
| 6,372,934 B1 * | 4/2002 | O'Lenick, Jr. et al. ....... 560/89 |
| 6,461,598 B1 * | 10/2002 | O'Lenick, Jr. et al. .... 424/70.1 |

* cited by examiner

*Primary Examiner*—Jyothsan Venkat

(57) ABSTRACT

The invention relates to a series of novel salt complexes that are made by neutralizing a fatty ammonium compound which is cationic with an anionic compound, producing a salt complex. The compounds of the present invention are water soluble, non-irritating to the eye and skin and are well suited to personal care applications.

14 Claims, No Drawings

WATER SOLUBLE CONDITIONING COMPLEXES

RELATED APPLICATION

This application is a continuation in part of application Ser. No. 09/483,899 filed Jan. 18, 2000 now U.S. Pat. No. 6,372,934 B1.

BACKGROUND OF THE INVENTION

1. Field of the Invention

The invention relates to a series of novel salt complexes that are made by neutralizing a fatty ammonium compound, which is cationic with an anionic compound, producing a salt-complex, and an inorganic salt. The compounds of the invention are water soluble, non-irritating to the eye and skin and are well suited to personal care applications.

2. Arts and Practices

Fatty quaternary compounds commonly called quats, are tetra-substituted ammonium compounds where each of the four groups on nitrogen are a group other than hydrogen. If any hydrogen groups are present, the compounds are not quaternary amines, but rather are primary or secondary amines.

The most commonly encountered substituents are alkyl and alkyl amido groups. There are several classes of quats. The most important are (a) alkyl tri methyl quats for example cetyltrimonium chloride, (b) alkylamidopropyl dimethyl quats like stearylamidoalkonium chloride and (c) di alkyl, di methyl quats for example dicetyldimonium chloride and (d) alkyl, benzyl, Di methyl quats like stearalkonium chloride.

There are several undesirable attributes of fatty cationic products.
1. Fatty Quaternary compounds are incompatible with anionic surfactants since an insoluble complex frequently is formed when the two types of materials are combined.
2. Many fatty Quaternary Compounds are eye irritants. The material is minim ally irritating to the eyes at concentrations of 2.5%, which limits the concentration, which is useful if low irritation is a requirement.
3. Fatty quats are generally hydrophobic and when applied to substrate can cause a loss of absorbance of the substrate. It is not an uncommon situation for a traveler to a hotel to encounter a very soft towel that totally fails to absorb water. This is because the fatty quaternary gives softness but being hydrophobic also prevents re-wet. This situation also can be observed on hair, the conditioner becomes gunky on the hair and has a tendency to build up.

We have learned that making complexes of cationic compounds (the so-called quaternary compounds) with carboxy fatty alcohol alkoxylates can unexpectedly mitigate many of these negative attributes. The preferred complex has to have a molecular weight of over 1000 molecular weight units to obtain the most effective irritation mitigation. The mitigation of irritation, the improved water solubility and the skin feel make the compounds of the present invention highly desirable in personal care applications. Combining these complexes with dimethicone copolyol polymers, produces products having low eye irritation, good skin feel and good emolliency. This makes the compounds ideally suited for ultra mild applications like baby shampoo and bubble bath applications.

THE INVENTION

Object of the Invention

It is the object of the present invention to provide a series of novel salt complexes that are made by neutralizing a fatty ammonium compound, which is cationic with an anionic compound, producing a salt-complex. The preferred complex has a molecular weight above 1000 molecular weight units. The compounds of the invention are water soluble, non-irritating to the eye and skin and are well suited to personal care applications, where low irritation is required.

An additional objective of the invention is to provide a process for conditioning hair and skin which comprises contacting the hair or skin with an effective conditioning concentration of the complex. The effective conditioning concentration is between 0.1 and 25% by weight of the formulation.

SUMMARY OF THE INVENTION

The invention relates to a series of novel salt complexes that are made by neutralizing a fatty ammonium compound, which is cationic with an anionic compound, producing a salt complex having a molecular weight above 1000 molecular weight units. The compounds of the invention are water soluble, non-irritating to the eye and skin and are well suited to personal care applications.

DETAILED DESCRIPTION OF THE INVENTION

The compounds of the present invention conform to the following structure:

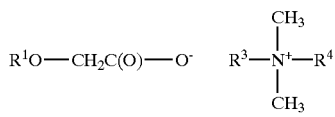

wherein;

$R^1$ is $CH_3-(CH_2)_n-O-(CH_2CH_2O)_a-(CH_2CH(CH_3)O)_b-(CH_2CH_2O)_c-$;

n is an integers ranging from 7 to 21;

a and c are integers independently ranging from 0 to 20, b is an integer ranging from 0 to 20;

$R^3$ is selected from the group consisting of $CH_3(CH_2)_e-$ and $R^5-C(O)N(H)-(CH_2)_3-$ $R^5$ is $CH_3(CH_2)_f-$ e is an integer from 5 to 21;

f is an integer from 5 to 21, $R^4$ is selected from the group consisting of $CH_3(CH_2)_g$ g is an integer ranging from 0 to 21 and

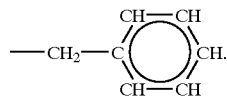

The invention is also directed to a process for conditioning hair and skin which comprises contacting the hair or skin with an effective conditioning concentration of a complex conforming to the following structure;

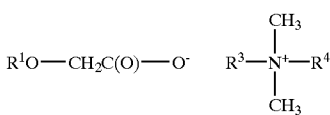

wherein;
R$^1$ is CH$_3$—(CH$_2$)$_n$—O—(CH$_2$CH$_2$O)$_a$—(CH$_2$CH(CH$_3$)O)$_b$—(CH$_2$CH$_2$O)$_c$—;
n is an integers ranging from 7 to 21;
a and c are integers independently ranging from 0 to 20;
b is an integer ranging from 0 to 20,
R$^3$ is selected from the group consisting of CH$_3$(CH$_2$)$_e$— and

R$^5$—C(O)N(H)—(CH$_2$)$_3$—

R$^5$ is CH$_3$(CH$_2$)$_f$—
e is an integer from 5 to 21;
f is an integer from 5 to 21;
R$^4$ is selected from the group consisting of CH$_3$(CH$_2$)$_g$
g is an integer ranging from 0 to 21 and

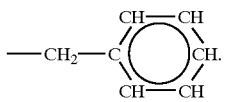

Preferred Embodiment

In a preferred embodiment R$^1$ is;

CH$_3$—(CH$_2$)$_n$—O—(CH$_2$CH$_2$O)$_a$—(CH$_2$CH(CH$_3$)O)$_b$—(CH$_2$CH$_2$O)$_c$—

In a preferred embodiment e is an integer ranging from 7 to 21.
In a preferred embodiment R$^3$ is;

R$^5$C(O)N(H)—(CH$_2$)$_3$— f is an integer ranging from 5 to 21.
In a preferred embodiment R$^4$ is methyl.
In a preferred embodiment R$^4$ is

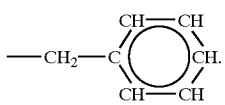

In a prefered embodiment the molecular weight of the complex is greater than 1000 daltons.
In another preferred embodiment, the complex is blended with dimethicone copolyol to improve the skin feel.

Examples of Reactants

Alcohol Alkoxy Carboxylate
The reaction sequence is illustrated by the reaction of an alcohol alkoxylate with sodium mono-chloroacetate:

R$^1$OH+Cl—CH$_2$C(O)O$^-$Na$^+$→R$^1$O—CH$_2$C(O)O$^-$Na$^+$

R$^1$O—CH$_2$C(O)O$^-$Na$^+$+H$^+$→R$^1$O—CH$_2$C(O)OH

R$^1$O—CH$_2$C(O)OH is the raw material useful in the preparation of the complexes of the present invention. The water can be removed by distillation and the salt filtered off.

Raw Materials

Carboxylates suitable for the preparation of the compounds of the present invention are commercially available from a variety of sources including Siltech Corporation in Toronto Ontario Canada.

| Example | n | a | b | c |
|---------|----|----|----|----|
| 1 | 8 | 0 | 0 | 0 |
| 2 | 10 | 0 | 1 | 12 |
| 3 | 12 | 20 | 10 | 20 |
| 4 | 14 | 3 | 1 | 3 |
| 5 | 16 | 20 | 20 | 20 |
| 6 | 18 | 12 | 0 | 0 |
| 7 | 20 | 12 | 1 | 1 |
| 8 | 22 | 5 | 0 | 5 |

Cationic Examples

The cationic compounds of the present invention are commercially available from a variety of sources including Croda Inc. and Siltech Corporation. They conform to the following structure:

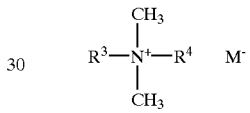

wherein;
R$^3$ is selected from the group consisting of

CH$_3$(CH$_2$)$_e$— and

R$^3$—C(O)N(H)—(CH$_2$)$_3$—

R$^5$ is CH$_3$(CH$_2$)$_f$—
e is an integer from 5 to 21;
f is an integer from 5 to 21;
R4 is selected from the group consisting of CH$_3$(CH$_2$)$_g$
g is an integer ranging from 0 to 21 and

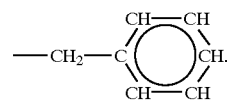

the group consisting of Cl$^-$, Br$^-$, and CH$_3$SO$_4^-$.

As used herein

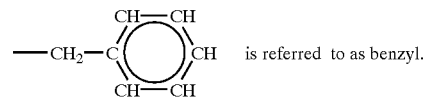  is referred to as benzyl.

EXAMPLES

Class 1 Cationic Compounds

| Example | e | g |
|---|---|---|
| 9 | 7 | 0 |
| 10 | 11 | 0 |
| 11 | 17 | 0 |
| 12 | 17 | 0 |
| 13 | 21 | 0 |
| 14 | 21 | benzyl |

M is Cl⁻

Class 2 Cationic Compounds

| Example | e | g |
|---|---|---|
| 15 | 7 | 7 |
| 16 | 11 | 7 |
| 17 | 15 | 21 |
| 18 | 17 | 3 |
| 19 | 21 | 5 |
| 20 | 17 | benzyl |
| 21 | 21 | benzyl |

M is Cl⁻

Class 3 Cationic Compounds
$R^3$ is $R^5C(O)N(H)—(CH_2)_3—$

| Example | f | g |
|---|---|---|
| 22 | 7 | 0 |
| 23 | 9 | 0 |
| 24 | 11 | 0 |
| 25 | 17 | 11 |
| 26 | 21 | 21 |
| 27 | 17 | Benzyl |
| 28 | 5 | 11 |

M is Cl⁻

Complexation

The carboxylate (examples 1–8) and the cationic compound (examples 9–28) are blended into water to make up a concentration of between 20–70% by weight. The preferred range is 30–50% by weight. The pH of the resulting mixture is then adjusted to between 5 and 9. The lower pH is preferred for skin care products, the higher for hair care products. The complex forms in aqueous solution and the counter ion on the cationic material remains in the solution as inorganic salt.

Example 29

To a suitable vessel is added 840.0 grams of water. Next 491.0 grams of carboxy compound Example 1 is added under agitation. Next 209.0 grams of cationic compound 9 is added. The pH is adjusted to 7.0 with KOH. The complex is used as prepared.

Examples 30–45

Example 29 is repeated, only this time the specified amount of water. Next the specified amount of the specified anionic compound is added. Next the specified amount of the specified cationic compound is added. The pH is adjusted to 7.0 with KOH. The complex is used as prepared.

| | Anionic Compound | | Cationic Compound | | Water |
|---|---|---|---|---|---|
| Example | Example | Grams | Example | Grams | Grams |
| 30 | 2 | 842.0 | 9 | 265.0 | 1328.0 |
| 31 | 3 | 2633.0 | 10 | 349.0 | 3578.0 |
| 32 | 4 | 547.0 | 11 | 373.0 | 1104.0 |
| 33 | 5 | 3279.0 | 12 | 405.0 | 4420.0 |
| 34 | 6 | 895.0 | 13 | 416.0 | 1704.0 |
| 35 | 7 | 1026.0 | 14 | 293.0 | 1582.0 |
| 36 | 8 | 863.0 | 15 | 349.0 | 1515.0 |
| 37 | 1 | 489.0 | 16 | 601.0 | 1635.0 |
| 38 | 2 | 840.0 | 17 | 377.0 | 1292.0 |
| 39 | 3 | 2631.0 | 18 | 416.0 | 3656.0 |
| 40 | 4 | 545.0 | 19 | 389.0 | 1167.0 |
| 41 | 5 | 3277.0 | 20 | 445.0 | 4466.0 |
| 42 | 6 | 893.0 | 21 | 280.0 | 1257.0 |
| 43 | 7 | 1024.0 | 22 | 308.0 | 1600.0 |
| 44 | 8 | 861.0 | 23 | 336.0 | 1436.0 |
| 45 | 5 | 3277.0 | 24 | 445.0 | 4466.0 |
| 46 | 6 | 893.0 | 25 | 280.0 | 1257.0 |
| 47 | 7 | 1024.0 | 26 | 308.0 | 1600.0 |
| 48 | 8 | 861.0 | 27 | 336.0 | 1436.0 |

Applications Evaluation

Control Compounds

Stearalkonium Chloride is an excellent conditioning agent, having outstanding substantivity to hair. It has detangling properties, improves wet comb when applied after shampooing. The FDA formulation data for 1976 reports the use of this material in 78 hair conditioners, eight at less than 0.1%, eighteen at between 0.1 and 1.0% and 52 at between 1 and 5%.

Cetyltrimonium Chloride, or CTAC, is a very substantive conditioner which in addition having a non-greasy feel, improves wet comb and also provides a gloss to the hair. It is classified as a severe primary eye irritant.[18] Therefore its use concentration is generally at or below 1%.

Eye Irritation

Eye irritation is a major concern in the formulation of personal care products, when working with quats. Primary eye irritation was tested using the protocol outlined in FHSLA 16 CFR 1500.42. The products were tested at 25% actives. The results were as follows:

Cationic Compounds (Not of the Present Invention)

| Product | Score | Result |
|---|---|---|
| Stearalkonium Chloride | 116.5 | Severely Irritating |
| Cetyltrimethyl ammonium Chloride | 106.0 | Severely Irritating |
| Cetyltriethyl ammonium Chloride | 115.0 | Severely Irritating |

Complexes of the Present Invention

| Product | Score | Result |
|---|---|---|
| Example 30 | 8.1 | Minimally Irritating |
| Example 31 | 11.3 | Minimally Irritating |
| Example 42 | 10.2 | Minimally Irritating |

-continued

| Product | Score | Result |
|---|---|---|
| Example 45 | 4.9 | Minimally Irritating |
| Example 46 | 7.8 | Minimally Irritating |

As the data clearly shows, the irritation potential of the complex is dramatically reduced, when compared to the starting quat.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A complex conforming to the following structure;

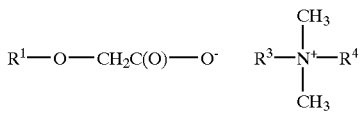

wherein;

$R^1$ is $CH_3-(CH_2)_n-O-(CH_2CH_2O)_a-(CH_2CH(CH_3)O)_b-(CH_2CH_2O)_c-$;

n is an integer ranging from 7 to 21;

a and c are integers independently ranging from 0 to 20, with the proviso that a+b be greater than 5;

b is an integer ranging from 0 to 20;

$R^3$ is selected from the group consisting of $CH_3(CH_2)_e-$ and $R^5-C(O)N(H)-(CH_2)_3-$ $R^5$ is $CH_3(CH_2)_f-$ e is an integer from 5 to 21;

f is an integer from 5 to 21;

$R^4$ is selected from the group consisting of $CH_3(CH_2)_g$ g is an integer ranging from 0 to 21 and

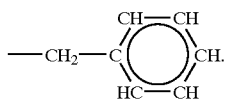

2. A complex of claim 1 wherein e is an integer ranging from 7 to 21.

3. A complex of claim 1 wherein $R^3$ is;

$R^5C(O)N(H)-(CH_2)_3-$.

4. A complex of claim 1 wherein f is an integer ranging from 5 to 21.

5. A complex of claim 1 wherein $R^4$ is methyl.

6. A complex of claim 1 wherein $R^4$ is

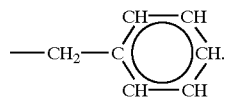

7. A process for conditioning hair and skin which comprises contacting the hair or skin with an effective conditioning concentration of a complex conforming to the following structure;

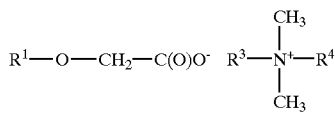

wherein;

$R^1$ is $CH_3-(CH_2)_n-O-(CH_2CH_2O)_a-(CH_2CH(CH_3)O)_b-(CH_2CH_2O)_c-$;

n is an integer ranging from 7 to 21;

a and c are integers independently ranging from 0 to 20, with the proviso that a+b be greater than 5;

b is an integer ranging from 0 to 20;

$R^3$ is selected from the group consisting of $CH_3(CH_2)_e-$ and $R^5-C(O)N(H)-(CH_2)_3-$ $R^5$ is $CH_3(CH_2)_f-$ e is an integer from 5 to 21;

f is an integer from 5 to 21;

$R^4$ is selected from the group consisting of $CH_3(CH_2)_g$ g is an integer ranging from 0 to 21 and

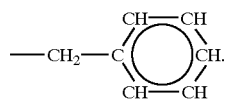

8. A process of claim 7 wherein said effective conditioning concentration ranges between 0.1 and 25% by weight.

9. A process of claim 7 wherein e is an integer ranging from 7 to 21.

10. A process of claim 7 wherein $R^3$ is;

$R^5C(O)N(H)-(CH_2)_3-$.

11. A process of claim 7 wherein f is an integer ranging from 5 to 21.

12. A process of claim 7 wherein $R^4$ is methyl.

13. A process of claim 7 wherein $R^4$ is

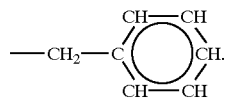

14. A process of claim 7 wherein the complex is blended with dimethicone copolyol.

* * * * *